US007875422B2

(12) United States Patent
Källander et al.

(10) Patent No.: US 7,875,422 B2
(45) Date of Patent: *Jan. 25, 2011

(54) VIRAL DRUG SUSCEPTIBILITY TESTING

(75) Inventors: Clas Källander, Uppsala (SE); Anders Malmsten, Uppsala (SE); Simon Gronowitz, Uppsala (SE); Xingwu Shao, Uppsala (SE)

(73) Assignee: Cavidi AB, Uppsala (SE)

( * ) Notice: Subject to any disclaimer, the term of this patent is extended or adjusted under 35 U.S.C. 154(b) by 1744 days.

This patent is subject to a terminal disclaimer.

(21) Appl. No.: 10/479,511

(22) PCT Filed: Jun. 14, 2002

(86) PCT No.: PCT/SE02/01156

§ 371 (c)(1),
(2), (4) Date: Dec. 10, 2003

(87) PCT Pub. No.: WO02/103040

PCT Pub. Date: Dec. 27, 2002

(65) Prior Publication Data

US 2004/0170958 A1 Sep. 2, 2004

Related U.S. Application Data

(60) Provisional application No. 60/297,764, filed on Jun. 14, 2001.

(51) Int. Cl.
*C12Q 1/25* (2006.01)
*A61K 39/21* (2006.01)

(52) U.S. Cl. .................... 435/5; 435/239; 424/207.1

(58) Field of Classification Search .............. 435/5, 435/7.92, 39, 69.2, 183, 199, 810
See application file for complete search history.

(56) References Cited

U.S. PATENT DOCUMENTS 4,707,439 A * 11/1987 Seto et al. .............. 435/5

FOREIGN PATENT DOCUMENTS

| WO | 9428115 A1 | 8/1994 |
| WO | 9732995 A1 | 12/1997 |
| WO | WO 01/01129 A2 * | 1/2001 |
| WO | 0175147 A1 | 11/2001 |

OTHER PUBLICATIONS

Vazquez-Rosales et al. Rapid Screening of Phenotypic Resistance to Nevirapine by Direct Analysis of HIV Type 1 Reverse Transcriptase Activity in Plasma, Nov. 13, 1999, Aids Research and Human Retroviruses, vol. 15, pp. 1191-1200.*
Rytting et al., Colorimetric Capture Assay for Human-Immunodeficiency-Virus-1 Reverse Transcriptase Activity, 1999, Biotechnology and Applied Biochemistry, vol. 29, pp. 241-250.*
Ventura et al., Effect of Nucleoside Analogs and Non-Nucleoside Inhibitors of HIV-1 Reverse Transcriptase on Cell-Free Virions, 1999, Archives of Virology, vol. 144, pp. 513-523.*
Woolf et al., Column-Switching High-Performance Liquid Chromatographic Determination of a 2-Pyridinnone-Based Human Immunodeficiency Virus Type 1 (HIV-1)-Specific Reverse Transcriptase Inhibitor in Human Plasma, Pharmaceutical Research, 1993, vol. 10, No. 1, pp. 56-60.*
Hertogs et al., Phenotypic and genotypic analysis of clinical HIV-1 isolates reveals extensive protease inhibitor cross-resistance: a survey of over 6000 samples. AIDS, Jun. 2000, vol. 14, No. 9, pp. 1203-1210.*
Hertogs et al., A Rapid Method for Simutaneous Detection of Phenotypic Resistanve to Inhibitors of Protease and Reverse Transcriptase in Recombinant Human Immunodeficiency Virus Type 1 Isolates from Patients Treated with Antiretroviral Drugs. Antimicrobial Agents and Chemotherapy, Feb. 1998, vol. 42, No. 2, pp. 269-276.*
Petropoulos et al. A novel phenotypic drug susceptibility assay for human immunodeficiency virus type 1. Antimicrobial Agents and Chemotherapy, Apr. 2000, vol. 44, No. 4, pp. 920-928.*
Davis et al. Conserved cysteines of the human immunodeficiency virus type 1 protease are involved in regulation of polyprotein processing and viral maturation of immature virions. Journal of Virology, Feb. 1999, vol. 73, No. 2, pp. 1156-1164.*
Zahler et al. A specific and sensitive assay for disulfides. The Journal of Biological Chemistry, Feb. 1968, vol. 243, No. 4, pp. 716-719.*
Chavan et al. Archives of Biochemistry and Biophysics, Dec. 1, 1995, vol. 324, No. 1, pp. 143-152.*
Kellam et al. Antimicrobial Agents and Chemotherapy, 1994, vol. 38, No. 1, pp. 23-30.*
Ekstrand et al. Biotechnological Applied Biochemistry, 1996, vol. 23, No. 2, pp. 95-105.*
Tummino et al. Antimicrobial Agents and Chemotherapy, Feb. 1997, vol. 41, No. 2, pp. 394-400.*
Bio Techniques, vol. 20, Feb. 1996, Raimond Lugert et al.: "Short Technical Reports: Specific Suppression of False-Positive Signals in the Product-Enhanced Reverse Transcriptase Assay", pp. 210-217.
National Library of Medicine (NLM), file Medline, Medline accession No. 10480632, Vazquez-Rosales G. et al., "Rapid screening of phenotypic resistance to nevirapine by direct analysis of HIV type 1 reverse transcriptase activity in plasma"; & AIDS research and human retroviruses, vol. 15, No. 13, Sep. 1, 1999, pp. 1191-1200.
Dev. Biol. Stand. Basel Karger, vol. 88, 1996, R.A. Metz et al., "The Reverse Transcriptase Assay: Problems and Practical Solutions", pp. 167-176.

* cited by examiner

*Primary Examiner*—Bo Peng
(74) *Attorney, Agent, or Firm*—Bacon & Thomas PLLC

(57) ABSTRACT

A method of testing phenotypic drug susceptibility in an enveloped virus-infected mammalian individual by testing on an enzyme packed into an enveloped virus, such as HIV, recovered from a biological sample, such as blood or plasma, from said individual is described. The method comprises the steps of a) adding an enzyme inactivating agent to the sample for inactivating polymerase activity other than that present in the enveloped virion, b) removing the enzyme inactivating agent, enzyme activity blocking antibodies, endogenous enzyme activity inhibitors and antiviral drugs, c) lysing the virus particle to release the enzyme, d) recovering the concentrated purified viral enzyme, such as a HIV reverse transcriptase (RT), resulting from c) and determining the drug sensitivity profile of the individual from the recovered enzyme by using sensitive enzyme assays. The drug sensitivity profile may be used for selecting drug treatment therapy. A commercial package is included.

7 Claims, 2 Drawing Sheets

VIRAL DRUG SUSCEPTIBILITY TESTING

Figure 1:
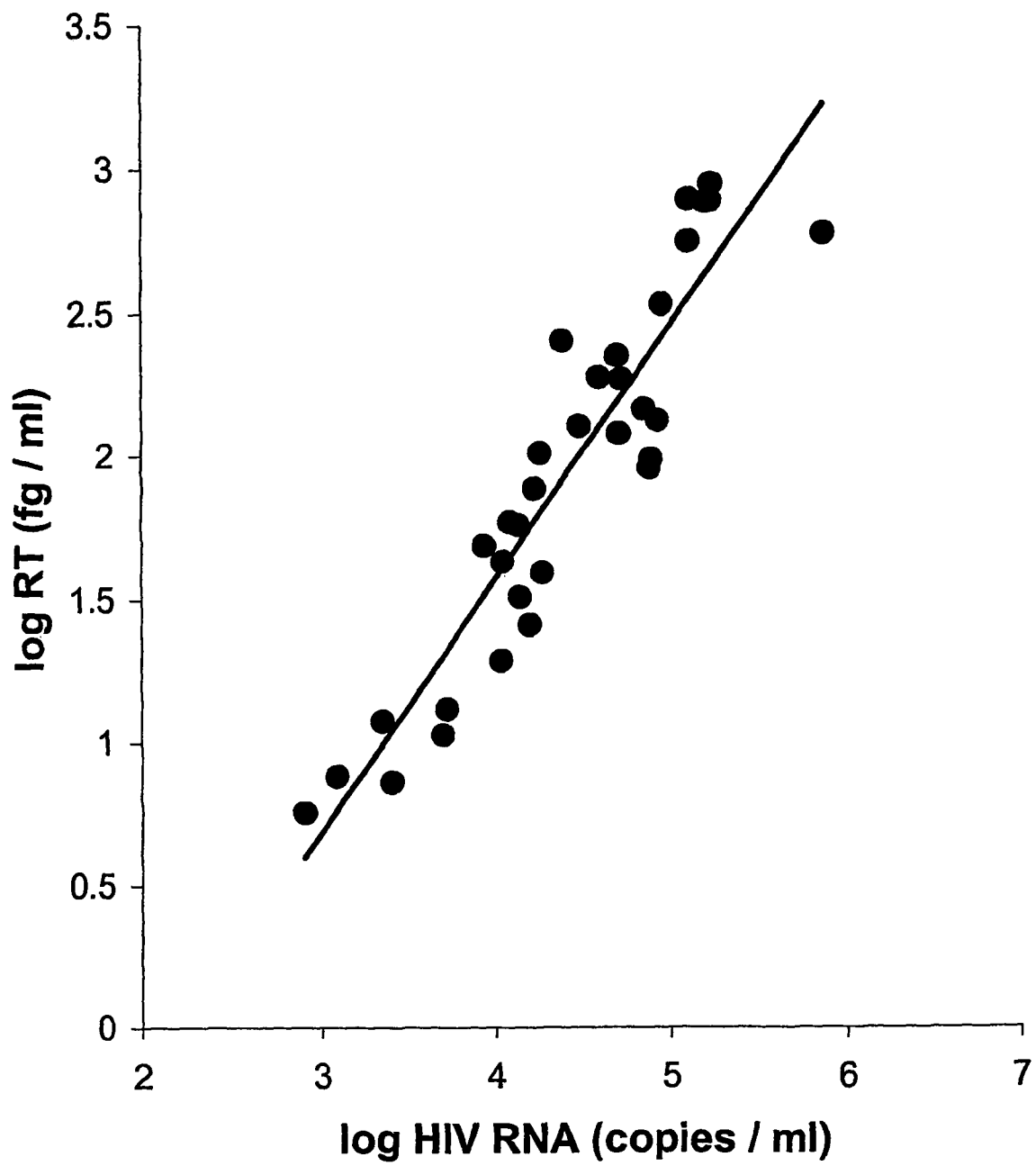

The present application is the United States National Phase of International Application PCT/SE02/01156 and claims benefit of provisional application No. 60/297,764, filed Jun. 14, 2001.

The present invention relates to viral drug susceptibility testing, in particular to a method of testing phenotypic drug susceptibility in a drug-treated enveloped virus-infected, such as retrovirus-infected, e.g. human immunodeficiency virus (HIV-1)-infected, mammalian individual by testing on an enzyme packed into an enveloped virus recovered from a biological sample from said individual.

BACKGROUND

HIV-drug susceptibility is associated with virologic response to new treatments. Standardized drug resistance tests are now available, and data from clinical trials suggest that the use of drug resistance testing may be associated with improved virologic outcome. However, drug resistance is complex in terms of performance, interpretation and clinical application.

Phenotypic tests measure the ability of an HIV isolate to grow in the presence of drug and is performed using assays in which the degree of virus replication inhibition at different drug concentrations is assessed. Results are used to calculate the 50% or 90% inhibitory concentration of a drug for an isolate. A potential problem with the classic phenotype assay is the effect of genetic drift in the virus population during virus isolation. In worst case the virus clone isolated is the one most fit to grow during in vitro conditions, not the one most abundant in the patient.

Measurement of phenotypic drug susceptibility can now be done via automated assays based on recombinant DNA technology. These approaches involve amplification of plasma RNA coding for HIV protease and reverse transcriptase (RT) and generation of a recombinant virus with the other genes from a laboratory construct (cassette virus) [1]. Genotype assays measure the occurrence of certain mutations in the genes targeted by antiretroviral drugs. Whereas phenotypic resistance measures virus-drug susceptibility, genotyping detects the mutations that confer phenotypic resistance. Polymerase chain reaction (PCR) amplification of HIV-1 sequences from plasma containing 500 to 1000 RNA copies per ml is the initial step in both these assays and in the recombinant virus phenotypic assays. Depending on mutations assessed and laboratory performing, the test, genotype assays may differentiate a mutant at a level of 10 to 50% in a mixture of viruses. The complexity of the data generated from sequencing has led to difficulties in interpreting the results. There may be varying interpretations regarding the level of phenotypic resistance conferred by a specific mutational pattern. As new data are generated, there is a risk of providing inadequate or even incorrect interpretations [2]. The reaction mechanism for all antiretroviral drugs used hitherto is in interference with the enzymatic reaction of either the viral protease or the RT. Depending on the capacity of the enzyme assays and the virus isolation techniques used, the drug sensitivity testing can theoretically be done either on supernatants from virus culture propagation, the primary virus isolation or on virus preparations recovered directly from the patients.

Drug susceptibility testing on RT from the primary virus isolation offers two advantages compared to traditional virus replication inhibition tests. The time for virus propagation is reduced and more important, less selection on the virus population will occur. The ideal situation is finally to characterize enzyme which has been extracted directly from the virus circulating in the blood of the patient. The benefit of such an approach is that the sample will mirror the virus population present in the patient at the time the blood sample was taken. This has so far not been feasible in practice, but the concept has been explored by resistance testing with the PCR based Amp RT assay [3].

The HIV-1 RT as well as other reverse transcriptases perform three different enzymatic reactions: RNA-dependent DNA polymerization, DNA-dependent DNA polymerization, and degradation of RNA in the DNA-RNA hybrid (RNase H). The HIV RT, encoded by the pol gene, is a heterodimer consisting of a p66 and a p51 subunit. Both RNA-dependent DNA polymerization and DNA-dependent DNA polymerization are performed by the same active site localized in the p66 subunit. The p51 is produced by removal of the C-terminal fragment of the p66 corresponding to the RNase H domain [4]. All RT inhibitors currently approved for clinical use inhibit the polymerase activity of the enzyme. The reaction mechanism of these drugs has mainly been defined according to their action on the RNA-dependent DNA polymerization reaction. The effect on the DNA-dependent DNA polymerization reaction is comparatively less studied.

Conventional RT activity assay is performed by utilising an artificial template-primer construction and labelled deoxynucleotide triphosphate as nucleotide substrate. The template/primer pair poly(rA)/oligo(dT) is the most efficient and most used combination for determination of HIV as well as for other retroviral RTs. A drawback of this type of assay when drug sensitivity testing is concerned, is that only non-nucleoside analogues or analogues that can base pair with rA can be tested. Analogues to the other nucleotide bases will require an assay based on a variable polymer template.

All anti-retroviral drugs approved hitherto interfere with the enzymatic reaction of either the viral protease or the RT. There are in addition candidate drugs in the pipeline which affect the function of the retroviral integrase.

The RT inhibitors are either nucleoside analogues or non-nucleoside analogues. The non-nucleoside inhibitors bind to a hydrophobic pocket in the RT enzyme close to, but not contiguous with the active site. HIV-1 replication is inhibited allosterically by displacing the catalytic aspartate residues relative to the polymerase binding site. Resistance usually emerges rapidly when non-nucleosides are administered as monotherapy or in the presence of incomplete virus suppression. Currently only three non-nucleoside inhibitors: Nevirapine, Efavirenz and Delavirdine are approved for clinical use by FDA.

The nucleoside inhibitors used today terminate the DNA chain elongation as they lack a 3'-hydroxyl group. Prolonged therapy with nucleoside inhibitors commonly leads to the development of resistant virus. This process is associated with the gradual appearance of mutations in the virus pol gene, each leading to defined amino acid substitutions [5]. The effects of these substitutions at the enzymatic levels are complicated and includes enhancement of a primitive DNA editing function. This reaction is nucleotide dependent and produces dinucleoside polyphosphate and an extendible DNA 3'end [6].

HIV therapy today is based on multidrug therapy. The regimens are based on combinations of all three types of drugs available: nucleoside analogues, non-nucleoside analogues and protease inhibitors. The strategy is to minimise the probability for a mutant virus to survive. Facing virologic failure current therapy guidelines recommend switch to an entirely new batch of drugs. This is frustrating since many HIV positive people do not have three or more untried drugs from which to choose. Further it may also be a wasteful decision to remove a drug that in fact still is effective. With improved drug resistance testing it might be possible to weed out the ineffective drug or drugs in a given combination.

DESCRIPTION OF THE INVENTION

The present invention provides a procedure to perform phenotypic drug resistance testing on enzyme that is recovered directly from patient plasma samples. It is based on a combination of techniques for recovering viral enzymes essentially free from their cellular counterparts followed by their measurement using sensitive enzyme assays. The enzyme isolation technique described can be used for any enzyme packed into an enveloped virus, but its use is in the present specification only explored by utilization of plasma derived RT for drug resistance testing.

Thus, one aspect of the invention is directed to a method of testing phenotypic drug susceptibility in an enveloped virus-infected mammalian individual by testing on an enzyme packed into an enveloped virus recovered from a biological sample from said individual, comprising the steps of
 a) adding an enzyme inactivating agent to the sample for inactivating polymerase activity other than that present in the enveloped virion,
 b) removing the enzyme inactivating agent, enzyme activity blocking antibodies, endogenous enzyme activity inhibitors and antiviral drugs,
 c) lysing the virus particle to release the enzyme,
 d) recovering the concentrated purified viral enzyme resulting from c) and determining the drug sensitivity profile of the individual from the recovered enzyme by using sensitive enzyme assays.

In an embodiment of the invention the mammalian individual is a human being.

In a presently preferred embodiment the biological sample is a blood sample, such as a plasma sample.

In another preferred embodiment the enveloped virus is a retrovirus, such as a human immunodeficiency virus (HIV). The enzyme is in the last mentioned case preferably a HIV reverse transcriptase (RT).

The drug sensitivity profile of an individual obtained with the method of the invention may be used for selecting drug treatment therapy for the individual. In practice, the enveloped virus-infected mammalian individual will be subjected to testing of the drug sensitivity profile at several points of time to monitor the development of the infection and the viral drug treatment in said individual.

The invention is also directed to a commercial package comprising written or data carrier instructions for testing phenotypic drug susceptibility in an enveloped virus-infected mammalian individual according to the invention, and an enzyme inactivating agent for inactivating polymerase activity, a sensitive enzyme assay, and at least one reference drug.

The invention will now be illustrated by the following unlimiting description of embodiments and drawings of the invention.

The teachings of the cited literature is incorporated herein by reference.

SHORT DESCRIPTION OF THE DRAWINGS

FIG. 1. shows the correlation between HIV-1 RT recovered and viral RNA measured with RNA PCR.

Figure 2:
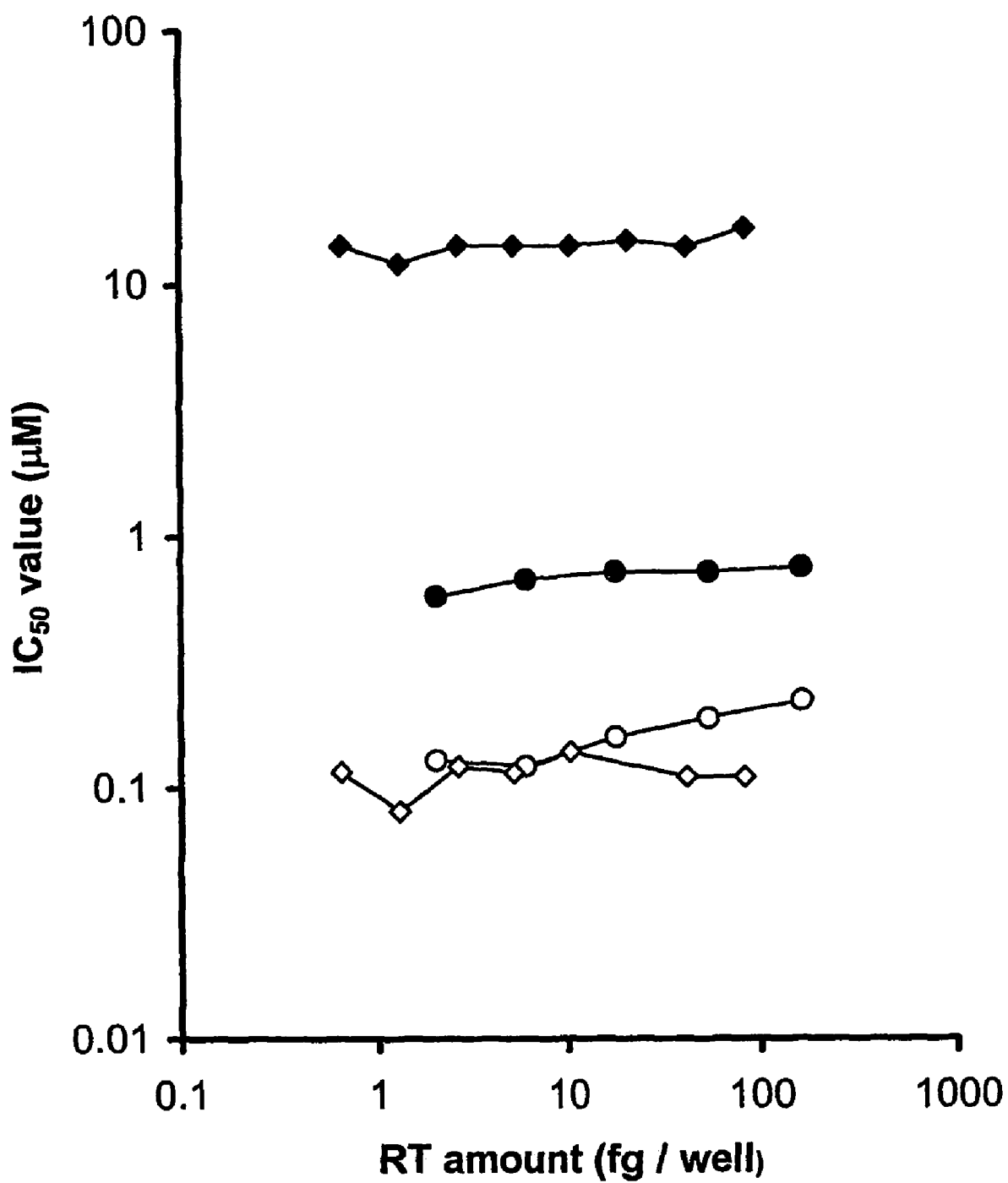

FIG. 2 exemplifies the relationship between the amount of RT used in the drug susceptibility assays and the $IC_{50}$ values found. Symbols: (◇) Efavirenz wild type RT, (♦) Efavirenz L100I RT, (○) AZT-TP wild type RT, (●) AZT-TP T215Y RT.

DESCRIPTION OF EMBODIMENTS

The procedure used consists of four different steps. I) Inactivation of host polymerase activity that is present in the sample without affecting the viral enzymes present in the enveloped virion. II) Removal of the enzyme inactivating agent, enzyme activity blocking antibodies, endogenous enzyme activity inhibitors and antiviral drugs. III) Recovering the concentrated purified viral enzyme. IV) Determining the drug sensitivity profile of the recovered enzyme.

(Steps I-III) Protocol for Isolation of Viral RT from Material which Contains RT Blocking Antibodies, Based on Destruction of Soluble Cellular Enzymes Followed by Isolation of Viral RT from Mini Columns.

1) Label the 4.5 ml plastic tubes to be used. Place them in a Nalgene box. Add 1 ml of sample (e.g. EDTA plasma from HIV infected individuals) to each labelled tube. Add 100 µl of a 66 mM solution of 5,5'-dithiobis-(2-nitrobenzoic acid) in buffered water, vortex and incubate the samples for one hour at room temperature.

The activity of the free plasma enzymes is destroyed during this procedure while the enzymes contained within the virions remain intact. The virions can then be purified from 5,5'-dithiobis-(2-nitrobenzoic acid), enzyme activity blocking antibodies and other substances that may interfere with quantification of viral RT by several separation procedures. The protocol below is based on the use of Fractogel® EMD TMAE Hicap gel.

2) Suspend the separation gel carefully and transfer 1500 µl gel slurry to each sample pretreatment tube.

3) Incubate the samples with the gel slurry for 90 minutes at room temperature with the tubes lying down horizontally on an orbital shaker.

4) Label the desired amount of 10 ml plastic mini columns to identify the samples being analyzed. Mount the columns in a column washing device i.e. a Supelco Visiprep solid phase extraction vacuum manifold. Transfer the contents in the binding tubes to their corresponding columns. Before transfer vortex the tube briefly to evenly distribute the gel.

5) When all the columns are filled, apply the vacuum and suck the gels dry. Turn off the vacuum and start the washing by filling each column with 9 ml buffer A. When all columns have been filled, apply the vacuum and suck the gels dry.

6) Repeat step 5 three more times, giving a total of four washes. Suck the gels dry after each wash. After sucking the gels dry after the fourth wash, turn off the vacuum and proceed to step 7.

The washing step removes unbound RT blocking antibodies and 5,5'-dithiobis-(2-nitrobenzoic acid) from the system.

7) Add to all dry gels 9 ml of conditioning buffer (B). After one minute apply vacuum and suck the gels dry.

8) Repeat step 7. Before turning off the vacuum check that all conditioning buffer (B) has been removed from all gels.

9) Lift off the upper part of the column wash device. Mount the tube holder with the labelled tubes into a clean container. Refit the upper part of the device. Control that the small tubings from each column go down in their corresponding tubes.

10) Add 600 µl lysis buffer (C) to each column. Let the buffer stand in the column for five minutes. Then apply the vacuum slowly and suck the gels dry. This will in each tube give approximately 600 µl of virus lysate from the connected gel.

The RT activity recovered in the lysates from step 10 are essentially free from RT blocking antibodies, drugs and cellular polymerase activity, and can be quantified with a sensitive RT activity assay, i.e. the Cavidi HS-kit Lenti RT, which is based on the method described by Ekstrand et al [7]. 25 µl lysate obtained according to the current protocol is sufficient for determination of the RT activity in the sample. The Remaining 575 µl sample should be frozen at −70° C. or below for later use in the drug sensitivity test.

Note: RT enzymes that are not sensitive to cystein modifying agents e.g. wild type HIV 1 RT can optionally be assayed in the presence of up to 5 mM 5,5'-dithiobis-(2-nitrobenzoic acid). Sensitive enzymes such as MULV RT and RT from certain therapy resistant HIV 1 strains (containing e.g. the mutation Y 181C) on the other hand require addition of a sulfhydryl reducing agent i.e. cystein or cysteamine to the lysis buffer.

(Step IV) Protocol for Determination of Drug Susceptibility of the RT Activity in the Lysates.

A modification of the calorimetric RT assay (Cavidi® HS-kit Lenti RT), available from Cavidi Tech, Uppsala, Sweden was used for the determination of the level of RT activity in the virus preparations studied. In short, poly(rA) covalently bound to the wells of a 96 well microtiter plate serves as template for the incorporation of 5-bromo-deoxyuridine 5'-triphosphate (BrdUTP) during the reverse transcription step at 33° C. The amount of bromodeoxyuridine monophosphate (BrdUMP) incorporated into DNA, is detected with an alkaline phosphatase (Ap) conjugated anti-BrdU monoclonal antibody. An Ap substrate, 4-methylumbelliferyl phosphate, is finally used for fluorimetric detection. The amount of isolate RT used in the $IC_{50}$ determinations was for the nucleoside analogues standardised to an activity corresponding to 5 fg ($4.3 \times 10^{-20}$ mol) reference HIV-1 RT per well, while 1.7 fg ($1.5 \times 10^{-20}$ mol) RT was used for the non-nucleoside analogues. The lysates were diluted in "mock lysates", i.e. lysates obtained from mock separation of foetal calf serum.

The RT inhibition studies were performed in two different modified versions of the HS Lenti RT assay.

The non-nucleoside analogues were serially diluted in five fold steps in RT reaction mixture and 25 µl aliquots were transferred to each well in the microtiter plate, mixed with 125 µl RT Reaction mixture and the enzyme reaction was initiated by addition of 25 µl lysate dilution. The final nucleotide substrate (BrdUTP) concentration was 16 µM and the primer ($odT_{22}$) amount 12 ng per well. The dT analogues were serially diluted in five fold steps in Chain-termination reaction mixture and 25 µl aliquots were transferred to each well in the microtiter plate, mixed with 125 µl RT Chain-termination reaction mixture and the enzyme reaction was initiated by addition of 25 µl lysate dilution. The final nucleotide substrate (BrdUTP) concentration was 1.5 µM and the primer ($odT_{22}$) amount 12 ng per well. For both nucleoside and non-nuclosides RT inhibitors the RT reaction was allowed to proceed over-night (16-24 hours at 33° C.). Thereafter the reaction was terminated by a wash of the plate. The $IC_{50}$ value was defined as the concentration of drug giving 50% inhibition of the RT activity studied.

Materials

Separation gel: e.g. Fractogel® EMD TMAE or Fractogel® EMD TMAE Hicap in 314 mM (2-(N-Morpholino)ethanesulfonic acid) (MES) pH 5.1, 413 mM Potassium iodide and Heparin 0.5 mg/ml.

Mini columns, e.g. Biorad Poly-Prep® (7311553)

Mini column washing device, i.e. Supelco Visiprep solid phase extraction vacuum manifold.

Plastic tubes, e.g. Nunc 4.5 ml cryogenic tubes.

Microtiter plates with immobilised prA, i.e. Nalge Nunc NucleoLinck®

Cysteine modifying agent, e.g. 66 mM 5,5'-dithiobis-(2-nitrobenzoic acid) in water buffered with 0.87 M Tris(hydroxymethyl)aminomethane (pH 8.3).

Mild sulfhydryl reducing agent, e.g. 33 mM cysteamine in water.

Antiviral Drugs:

3'-azido-2',3'-deoxythymidine triphosphate (AZT-TP) and (2',3'-didehydro-3'-deoxythymidine triphosphate (d4T-TP) was bought from Moravek Biochemicals, California. Nevirapine (11-cyclopropyl-5,11-dihydro-4-methyl-6H-dipyrido [3,2-b:2',3'-f][1,4]diazepin-6-one) (NVP), Delaviridine, 1-(5-methanesulphonamido-1H-indol-2-yl-carbonyl)-4-[3-(1-methylethyl-amino)pyridinyl]piperazine monomethane sulphonate (DLV) and Efavirenz, (−)6-chloro-4-cyclopropylethynyl-4-trifluoromethyl-1,4-dihydro-2H-3,1-benzoxazin-2-one) (EFV) were bought from Apoteksbolaget, Uppsala, Sweden.

Plasma Samples from HIV Infected Individuals.

Plasma samples from naïve treatment patients or from patients treated with ordinary combination therapy were selected retrospectively. The coded samples were delivered frozen as two different panels, representing patients with resistance to NNRTIs and to T-analogues respectively. The amount of HIV-1 RNA in each sample was measured by standard HIV 1 RNA PCR (Cobas, Roche Diagnostica) and the viral genotype present was analyzed with TRUGENE™ HIV-1 Genotyping kit. (Visible Genetics).

Recombinant RT Enzymes:

NNRTI resistant mutant forms of RT were produced (L100I, K103N, L100I/K103N, Y181C). As template for the mutations was used the pETRT expression vector, which was constructed from the BH10 isolate. Mutations were generated using commercial site-directed mutagenesis kits, QuikChange (Stratagene). The mutations were verified by DNA sequence analysis. The mutated and native forms of RT were isolated as previously described [8].

The recombinant RTs with AZT specific mutations were produced by introducing the mutation into the RT-coding region of a wild type HXB2-D EcoRI-NdeI restriction enzyme fragment cloned into the expression vector pKK233-2 (Amersham Biotech). Mutations were generated using commercial site-directed mutagenesis kits, QuikChange (Stratagene). The mutated cloned expression vectors were transformed into E. coli strain XL1-Blue and the genotypes were verified by DNA sequence analysis.

Buffers Used:
A) Wash buffer: 20 mM MES pH 5.4, 500 mM Potassium acetate (KAc)
B) Conditioning buffer. An RT assay compatible buffer e.g. 50 mM (N-(2-Hydroxyethylpiperazine-N'-(2-ethanesulfonic acid) (Hepes) pH 7.6, KAc 25 mM, magnesium chloride ($MgCl_2$) 20 mM, EthyleneGlycol-bis(β-aminoethyl Ether) N,N,N',N'-Tetraacetic Acid (EGTA) 0.2 mM, spermine 2 mM and heat inactivated bovine serum albumin (BSA) 0.5 mg/ml.
C) Lysis buffer: An RT assay compatible buffer including a detergent e.g. 1.25% Polyoxyethylene 4 Lauryl Ether (Brij 30), 13 ng/ml $odT_{22}$ and the same components as in the conditioning buffer (B). A sulfhydryl reducing agent, i.e. 0.2 mM cysteamine is optionally added when processing viruses with RT that are sensitive to SH oxidation/modification.

D) RT Reaction mixture e.g. 10 mM Hepes pH 7.6, 19 μM BrdUTP, 80 ng/ml odT$_{22}$, 4 mM MgCl$_2$, 0.5 g/l dextrane sulphate, 2 mM spermine, Triton-X 100 0.5%(v/v), EGTA 0.2 mM and BSA 0.5 mg/ml.

E) Chain-termination reaction mixture: Hepes 10 mM pH 7.0, BrdUTP 1.75 μM, odT$_{22}$ 80 ng/ml, MgCl$_2$ 10 mM, ATP 7 mM, dextrane sulphate 0.05 g/l, spermine 2 mM, Triton-X 100 0.5%(v/v), EGTA 0.2 mM and BSA 0.5 mg/ml.

EXAMPLES

Example 1

Correlation Between HIV-1 RT Recovered and Viral RNA Measured with RNA PCR 1 ml samples of EDTA plasma from HIV infected individuals were processed according to "Protocol for isolation of viral RT from material which contains RT blocking antibodies, based on destruction of soluble cellular enzymes followed by isolation of viral RT from mini columns." and the amount of RT activity recovered from each sample was determined in an overnight RT assay using Cavidi® HS-kit Lenti RT. The RT activities obtained were recalculated into fg HIV 1 RT/ml plasma according to an internal standard curve. The amount of HIV 1 RNA in each sample was measured by standard HIV 1 RNA PCR (Roche Amplicor). The plot is restricted to samples with PCR values >500 copies/ml. A strong correlation was found between amount of plasma RT recovered and amount of HIV RNA measured with PCR (r=0.93, n=33, p<<0.001). See FIG. 1.

From the example it can be extracted that processing of 1 ml plasma from an individual with 50 000 HIV RNA copies per ml plasma will result in recovery of approximately 200 fg RT activity. Using 1.7 fg RT per test this amount corresponds to 118 tests, which can be used for determination of the drug sensitivity profile of the isolated RT.

Example 2

Influence of the Amount of RT Used in the Drug Susceptibility Tests

The effects of NNRTIs, AZT-TP and d4T-TP on indicated recombinant HIV 1 RT were determined according to "Protocol for determination of drug susceptibility of the RT activity in the lysates" using indicated RT concentrations. FIG. 2 exemplifies the relation between the amount of RT used in the drug susceptibility assays and the IC$_{50}$ values found. The IC$_{50}$ values for NNRTIs like Efavirenz was not at all influenced by variations in the RT amount within the range investigated. Among the NRTIs studied AZT-TP exhibit the largest variation in relation to the amount of RT included in the assay. This variation was maximal for wild type RT and the IC$_{50}$ increased from 0.13 to 0.22 μM when increasing the RT amount from 2 to 162 fg/well (FIG. 2).

The amount of RT activity available in the plasma samples sets the limits of the current tests. A signal at least five times background is required to obtain reproducible IC$_{50}$ values for the drugs tested. The low variability of the IC$_{50}$ values when increasing RT amounts are added to the test makes drug sensitivity determination feasible without previous standardization of the amount of RT used in each assay.

Example 3

Comparison of the Effects of Non-Nucleoside Inhibitors on Recombinant HIV 1 RT with Defined Mutations The effects of three non-nucleoside inhibitors on indicated recombinant HIV 1 RT were determined according to "Protocol for determination of drug susceptibility of the RT activity in the lysates." The amount of each RT was standardized to correspond to the activity of 1.7 fg/well of our reference RT. The duration of the RT reaction was 19 hours and the activities obtained were recalculated into % of the activity with the same RT incubated in absence of inhibitor.

The phenotype data was extracted from the literature (International antiviral news and http://stanford.edu/hiv database) (Table 1).

There was in general a strong correlation between the IC$_{50}$ values from the RT inhibition assay and the phenotype data according to the literature. It was always possible to discern RTs from highly or intermediate resistant virus (Table 1).

Example 4

Comparison of the Effect of dT Anlogues on Recombinant HIV 1 RT with Defined Mutations The effects of AZT-TP and d4T on indicated recombinant HIV 1 RT were determined according to "Protocol for determination of drug susceptibility of the RT activity in the lysates." The amount of each RT was standardized to correspond to the activity of 5 fg/well of our reference RT. The duration of the RT reaction was 19 hours and the activities obtained were recalculated into % of the activity with the same RT incubated in absence of inhibitor.

The phenotype data was extracted from the literature (International antiviral news and http://stanford.edu/hiv database) (Table 2).

The Chain-termination reaction mixture used for the determination of susceptibility to T-analogue drugs should be able to support an energy dependent phosphorolysis reaction. Regrettably an efficient phosphorolysis reaction is promptly reflected by a decrease in polymerization velocity and as a consequence also a decrease in detection sensitivity. Therfore this assay require more RT activity, compared to the corresponding assay for the NNRTIs. Another consequence is that the span between resistant and sensitive RTs is smaller than in the NNRTI assay. However, there was in general a strong correlation between the IC$_{50}$ values from the RT inhibition assay and the phenotype data according to the literature. It was always possible to discern RTs from highly or intermediate resistant virus. (Table 2).

Example 5

Determination of the susceptibility to NNRTIs using plasma derived RTs. One ml samples of plasma from 17 HIV infected individuals from Stockholm, Sweden were processed according to "Protocol for isolation of viral RT from material which contains RT blocking antibodies, based on destruction of soluble cellular enzymes followed by isolation of viral RT from mini columns." 15 of these contained enough RT to allow drug susceptibility testing. The PCR value for these samples was 17 000 copies/ml or larger. Each plasma RT and two control enzymes were titrated towards a set of serial dilutions of Nevirapine, Efavirenz, and Delavirdine according to Protocol for determination of drug susceptibility of the RT activity in the lysates.

Using an activity corresponding to 1.7 fg/well reference RT HIV-1 RT from each RT extract we found that 7 of the 15 samples contained RTs that were highly resistant to all three NNRTIs (Table 3). All had the substitution K103N or in one case (sample 656) the combination of the substitutions A98G and Y181C in their RT genes. Eight samples were sensitive to all three NNRTIs. Six of which had no relevant mutation in their RT genes while the remaining two had either V179I or V179T/A/I mutations, which not is known to affect the sensitivity to NNRTIs.

Example 6

Determination of the Susceptibility to AZT-TP and d4T-TP using Plasma Derived RTs One ml samples of plasma from 27 HIV infected individuals from Stockholm, Sweden were processed according to "Protocol for isolation of viral RT from material which contains RT blocking antibodies, based on destruction of soluble cellular enzymes followed by isolation of viral RT from mini columns." Only 13 of these contained enough RT to allow drug susceptibility testing. The PCR value for these samples was 43 000 copies/ml or larger. Each plasma RT and two control enzymes were titrated towards a set of serial dilutions of AZT-TP and d4T-TP according to Protocol for determination of drug susceptibility of the RT activity in the lysates. See Table 4.

Using an activity corresponding to 5 fg/well reference RT HIV-1 RT from each RT extract and the Chain-termination reaction mixture we found that the $IC_{50}$ values for both drugs increased in parallel with accumulation of mutations known to be involved in resistance to NRTIs (Table 4). The mutations D69N or M184V alone did as expected not result in increased $IC_{50}$ values. Sample 656 and 1320 contained RTs which in spite of presence of several amino acid substitutions known to affect resistance to NRTIs exhibited intermediate $IC_{50}$ values for both AZTT-TP and d4T-TP. These isolates were found to also contain Y181C or Ml84V substitutions which are known to cause resensitation towards T-analogue drugs. Two RTs in the current panel exhibited $IC_{50}$ values which were elevated at least 20 times compared to the wild type control RT (Table 4). One of these had a set of amino acid (aa) insertions representative for the Q151M complex [8] and the other contained the classic K70R substitution and in addition a L210S substitution. Using the $IC_{50}$ values 1 µM and 0.1 µM as cut of values for AZT-TP and d4T-TP respectively the extracts can be classified as containing 9 sensitive and 4 resistant RTs, which is in concordance with the results from the genotype assay.

REFERENCES

1. Petropoulos C J, Parkin N T, Limoli K L, Lie Y S, Wrin T, Huang W, Tian H, Smith D, Winslow G A, Capon D J, Whitcomb J M. A novel phenotypic drug susceptibility assay for human immunodeficiency virus type 1. Antimicrob Agents Chemother. 2000 April; 44(4):920-8.

2. The Euroguidelines Group for HIV resistance. Clinical and laboratory guidelines for the use of HIV-1 drug resistance testing as part of treatment management: recommendations for the European setting. AIDS. 2001 Feb. 16; 15(3): 309-20.

3. Vazquez-Rosales G, Garcia Lerma J G, Yamamoto S, Switzer W M, Havlir D, Folks T M, Richman D D, Heneine W. Rapid screening of phenotypic resistance to nevirapine by direct analysis of HIV type 1 reverse transcriptase activity in plasma. AIDS Res Hum Retroviruses. 1999 Sep. 1; 15(13):1191-200.

4. Goff, S. P. (1990) Retrovirus reverse transcriptase: Synthesis, Structure, and Function. Review. J Acquir 1 mm Defic Syndr 3: 817-831.

5. Vandamme A M, Van Vaerenbergh K, De Clercq E. Antihuman immunodeficiency virus drug combination strategies. Antivir Chem Chemother. 1998 May; 9(3):187-203.

6. Meyer P R, Matsuura S E, Mian A M, So A G, Scott W A. Related Articles. A mechanism of AZT resistance: an increase in nucleotide-dependent primer unblocking by mutant HIV-1 reverse transcriptase. Mol Cell. 1999 July; 4(1):35-43

7. Ekstrand D H, Awad R J, Källander C F, Gronowitz J S. A sensitive assay for the quantification of reverse transcriptase activity based on the use of carrier-bound template and non-radioactive-product detection, with special reference to human-immunodeficiency-virus isolation. Biotechnol Appl Biochem. 1996 April; 23 (Pt 2):95-105.

8. Lindberg J; Sigurethsson S, Löwgren S, O Andersson H, Sahlberg C, Noreen R, Fridborg K, Zhang H, Unge T. Structural basis for the inhibitory efficacy of efavirenz (DMP-266), MSC194 and PNU142721 towards the HIV-1 RT K103N mutant. Eur J Biochem. 2002 March; 269(6): 1670-1677

9. Shirasaka, T., Kavlick, M. F., Ueno, T., Gao, W.-Y., Kojima, E., Alcaide, M. L., Chokekijchai, S., Roy, B. M., Arnold, E., Yarchoan, R., and Mitsuya, H. Emergence of human immunodeficiency virus type 1 variants with resistance to multiple dideoxynucleosides in patients receiving therapy with dideoxynucleosides. Proc Natl Acad Sci USA 1995, 92:2398-2402.

10. Larder B A. 3'-Azido-3'-deoxythymidine resistance suppressed by a mutation conferring human immunodeficiency virus type 1 resistance to nonnucleoside reverse transcriptase inhibitors. Antimicrob Agents Chemother. 1992 December; 36(12):2664-9.

11. Larder B A. Interactions between drug resistance mutations in human immunodeficiency virus type 1 reverse transcriptase. J Gen Virol. 1994 May; 75 (Pt 5):951-7.

12. Boucher C A, Cammack N, Schipper P, Schuurman R, Rouse P, Wainberg M A; Cameron J M. High-level resistance to (−) enantiomeric 2'-deoxy-3'-thiacytidine in vitro is due to one amino acid substitution in the catalytic site of human immunodeficiency virus type 1 reverse transcriptase. Antimicrob Agents Chemother. 1993 October; 37(10):2231-4

TABLE 1

Comparison of the effect of non-nucleoside inhibitors on recombinant HIV 1 RT with defined mutations.

| Modification in RT analysed | IC$_{50}$ of indicated inhibitor in RT assay (μM) | | | Sensitivity of the corresponding virus* | | |
|---|---|---|---|---|---|---|
| | Nevirapin | Delaviridine | Efavirienz | Nevirapin | Delaviridine | Efavirienz |
| L100I | 32 | 9.5 | >4 | L | I | I |
| K103N | >100 | 3.0 | >4 | H | H | H |
| L100I/K103N | >100 | >100 | >4 | H | H | H |
| Y181C | >100 | 3.0 | 0.5 | H | H | L |
| wild type BH10 | 0.2 | 0.5 | 0.04 | S | S | S |
| wild type HxB2 | 1.7 | 1.6 | 0.12 | S | S | S |

*Phenotype data:
S = sensitive,
L = Low level resistance (2–10 times increase in inhibitory dose),
I = Intermediate resistance (10–100 times increase),
H = High level resistance (>100 times increase).
$^a$nd not done.

TABLE 2

Comparison of the effect of AZT-TP and d4T on recombinant HIV 1 RT with defined mutations.

| Modification in RT analyzed* | IC$_{50}$ of AZT-TP in RT assay (μM) | IC$_{50}$ of d4T-TP in RT assay (μM) | Sensitivity of the corrsponding virus*. | |
|---|---|---|---|---|
| | | | AZT | d4T |
| T215Y | 0.69 | 0.15 | I | L |
| M41L/T69S-SS/ L210W/ R211K/L214F/ T215Y | 4.0 | 0.49 | H | H |
| wild type HXB2 | 0.19 | 0.050 | S | S |
| wildtype BH 10 | 0.16 | 0.033 | S | S |
| Y181C | 0.15 | 0.033 | RS | RS |

*Phenotype data:
RS = the mutations gives re-sensitation of resistant virus.
S = sensitive,
L = Low level resistance,
I = Intermediate resistance,
H = High level resistance.
$^a$nd not done..

TABLE 3

Effect of NNRTIs on HIV RT recovered from patient plasma

| Patient code | PCR value | fg RT/ml plasma | IC$_{50}$ NVP (μM) | IC$_{50}$ EPV (μM) | IC$_{50}$ DLV (μM) | 98 A | 101 L | 103 K | 106 V | 108 V | 179 V | 181 Y |
|---|---|---|---|---|---|---|---|---|---|---|---|---|
| 3980 | 542 000 | 1056 | 0.65 | 0.09 | 7.51 | | | | | | * | |
| 1177 | 73 000 | 83 | 0.81 | 0.17 | 4.54 | | | | | | | |
| 1412 | 17 000 | 40 | 0.80 | 0.21 | 3.60 | | | | | | | |
| 1784 | 17 000 | 69 | 0.97 | 0.15 | 8.22 | | | | | | I | |
| 1885 | 465 000 | 1032 | 0.97 | 0.17 | 8.97 | | | | | | | |
| 1572 | 105 000 | 146 | 2.16 | 0.21 | 9.54 | | | | | | | |
| 1424 | 245 000 | 375 | 2.92 | 0.42 | 8.21 | | | | | | | |
| 1639 | 431 000 | 71 | 3.14 | 0.33 | 12.7 | | | | | | | |
| 494 | 18 000 | 39 | >100 | >4 | >100 | S | I | N | | | | |
| 622 | 529 000 | 400 | >100 | >4 | >100 | | I | N | | | | |
| 2098 | >750 000 | 5533 | >100 | >4 | >100 | | | N | | H | | |
| 2883 | 71 000 | 517 | >100 | >4 | >100 | | I | N | | | | |
| 3807 | 764 000 | 683 | >100 | >4 | >100 | | I | N | | | | |

TABLE 3-continued

Effect of NNRTIs on HIV RT recovered from patient plasma

| | | | | | | Mutations at amino acid | | | | | | |
|---|---|---|---|---|---|---|---|---|---|---|---|---|
| Patient code | PCR value | fg RT/ml plasma | $IC_{50}$ NVP (μM) | $IC_{50}$ EPV (μM) | $IC_{50}$ DLV (μM) | 98 A | 101 L | 103 K | 106 V | 108 V | 179 V | 181 Y |
| 656 | >75 000 | 1921 | >100 | >4 | >100 | G | | | | | | C |
| 1517 | 353 000 | 268 | >100 | >4 | >100 | | | N | | | | |
| Recombinant RT controls | | | | | | | | | | | | |
| L100I | | | 32 | >4 | 9.5 | | I | | | | | |
| wild type RT | | | 1.7 | 0.12 | 1.6 | | | | | | | |

*Hetrogenicity in the sequence V179T/A/I.

TABLE 4

Effect of AZT-TP and d4T-TP on HIV RT recovered from patient plasma

| | | | AZT-TP $IC_{50}$ | d4T-TP | Mutations at amino acid | | | | | | | | | | | | | |
|---|---|---|---|---|---|---|---|---|---|---|---|---|---|---|---|---|---|---|
| Patient code | PCR value | fg RT/ ml plasma | (μM)/fold increase | $IC_{50}$ (μM)/fold increase | 41 M | 44 E | 67 D | 69 T | 70 K | 210 L | 215 T | 219 K | 75 V | 116 F | 118 V | 151 Q | 181 Y | 184 M |
| 3507* | 54 000 | 83 | 0.13    0.8 | 0.020    0.6 | | | | | | | | | | | | | | |
| 622 | 529 000 | 400 | 0.23    1.4 | 0.028    0.8 | | N | | | | | | | | | | | | |
| 160 | 363 000 | 350 | 0.27    1.7 | 0.043    1.3 | | | | | | | | | | | | | | |
| 2098 | >750 000 | 5533 | 0.35    2.2 | 0.048    1.5 | | | | | | | | | | | | | | |
| 48 | 189 000 | 30.8 | 0.47    2.9 | 0.085    2.6 | | | | | | | | | | | | | | |
| 181 | 550 000 | 831 | 0.50    3.1 | 0.049    1.5 | | | | | | | | | | | | | | |
| 807 | 420 000 | 294 | 0.50    3.1 | 0.070    2.7 | | | | | | | | | | | | | | |
| 662 | 750 000 | 4567 | 0.50    3.1 | 0.065    2.0 | | | | | | | | | | | | | | |
| 1144 | 110 000 | 76.7 | 0.56    3.5 | ND# | | | | | | | | | | | | | | V |
| 656* | >75 000 | 1921 | 1.25    7.8 | 0.17    5.2 | L | D | N | | | W | Y | | | | I | | C | |
| 1320* | 43 000 | 420 | 1.32    8.3 | 0.59    19.6 | | | | | | W | Y | | | | I | | | V |
| 393 | 750 000 | 388 | 3.2    20 | 0.42    12.7 | | | | | | | | | X | Y | | M | | |
| 1030 | 207 000 | 173 | 3.2    20 | 1.1    33 | | | | | R | S | | | | | | | | |
| Recombinant RT controls | | | | | | | | | | | | | | | | | | |
| wild type RT | | | 0.16    1.0 | 0.033    1.0 | | | | | | | | | | | | | | |
| T69S→SS$^a$ | | | 4.00    25 | 0.49    15 | L | | | S-SS | | W | Y | | | | | | | |

Not determined due to irregularities in profile.
*The RT in sample 656 had both a L100I and a 181C substitution which are known to give resensitation (See refs. 10 and 11). The RT in sample 1320 had a M184V substitution which is known to give re-sensitation (See ref.12).
$^a$This RT contains an T69S→SS insertion..
$^a$This RT contains an T69S→SS insertion.

The invention claimed is:

1. A method of testing phenotypic drug susceptibility of a retrovirus in a mammalian individual infected by said retrovirus by testing a reverse transcriptase packed inside the retrovirus particle, comprising the steps of
   a) obtaining a biological sample from said individual;
   b) adding a cysteine modifying agent to said biological sample for inactivating polymerase activity present in said sample other than that present inside said retrovirus particle, wherein the cysteine modifying agent is 5,5'-dithiobis-(2-nirobenzoic acid);
   c) removing enzyme activity blocking antibodies, endogenous enzyme activity inhibitors, and antiviral drugs present in said biological sample, as well as said cysteine modifying agent, thereby obtaining the purified retrovirus particle;
   d) lysing the retrovirus particle to release said reverse transcriptase packed inside said retrovirus particle;
   e) recovering said reverse transcriptase essentially free from its cellular counterparts resulting from steps b) through d); and
   f) assaying the activity of the recovered reverse transcriptase by using a polymerase assay, and determining the drug sensitivity profile of said individual.

2. The method according to claim 1, wherein the mammalian individual is a human being.

3. The method according to claim 1, wherein the biological sample is a blood sample.

4. The method according to claim 3, wherein the blood sample is a plasma sample.

5. The method according to claim 1, wherein the retrovirus is a human immunodeficiency virus (HIV), and the reverse transcriptase is a HIV reverse transcriptase.

6. The method according to claim 1, wherein the drug sensitivity profile of the individual is used for selecting drug treatment therapy for the individual.

7. The method according to claim 2, wherein the biological sample is a blood sample.

* * * * *